(12) United States Patent
Rong et al.

(10) Patent No.: US 12,414,755 B2
(45) Date of Patent: Sep. 16, 2025

(54) DUAL MODE THREE-DIMENSIONAL BREAST IMAGING DEVICE AND METHOD

(71) Applicant: DOBI Global, LLC, Southborough, MA (US)

(72) Inventors: Ruowen Rong, Southborough, MA (US); Hongtao Wang, Hangzhou (CN); Ye Wu, Hangzhou (CN); John G. Zhang, Southborough, MA (US)

(73) Assignee: DOBI Global, LLC

( * ) Notice: Subject to any disclaimer, the term of this patent is extended or adjusted under 35 U.S.C. 154(b) by 98 days.

(21) Appl. No.: 17/980,321

(22) Filed: Nov. 3, 2022

(65) Prior Publication Data

US 2023/0146520 A1 May 11, 2023

Related U.S. Application Data

(60) Provisional application No. 63/276,345, filed on Nov. 5, 2021.

(51) Int. Cl.
*A61B 8/00* (2006.01)
*A61B 5/00* (2006.01)
*A61B 8/08* (2006.01)

(52) U.S. Cl.
CPC .......... *A61B 8/4416* (2013.01); *A61B 5/0073* (2013.01); *A61B 5/0091* (2013.01); *A61B 8/0825* (2013.01); *A61B 8/5261* (2013.01)

(58) Field of Classification Search
CPC ... A61B 8/4416; A61B 8/0825; A61B 8/5261; A61B 5/0073; A61B 5/0091
See application file for complete search history.

(56) References Cited

U.S. PATENT DOCUMENTS

| | | | | |
|---|---|---|---|---|
| 2009/0171195 A1* | 7/2009 | Barbour | ............. | A61B 5/14551 600/425 |
| 2013/0190595 A1* | 7/2013 | Oraevsky | ............... | A61B 8/483 600/407 |
| 2017/0156662 A1* | 6/2017 | Goodall | ................. | A61N 2/002 |

FOREIGN PATENT DOCUMENTS

CN           109008986 A    * 12/2018

OTHER PUBLICATIONS

Zalev et al.; "Opto-acoustic imaging of relative blood oxygen saturation and total hemoglobin for breast cancer diagnosis"; Journal of Biomedical Optics 24(12), 121915 (Dec. 2019) (Year: 2019).*
Oraevsky et al.; "Clinical optoacoustic imaging combined with ultrasound for coregistered functional and anatomical mapping of breast tumors"; Photoacoustics 12 (2018) pp. 30-45 (Year: 2018).*
Vavadi et al. "Compact ultrasound-guided diffuse optical tomography system for breast cancer imaging" (Year: 2018).*

* cited by examiner

*Primary Examiner* — Dixomara Vargas
(74) *Attorney, Agent, or Firm* — Barclay Damon LLP; Jerry Cohen

(57) ABSTRACT

A method and apparatus for dual mode imaging uses an ultrasonic detection device, a diffuse optical tomography (DOT) detection device for imaging a breast. The DOT detection device is configured to detect changes of tissue blood oxygen. A host machine in communication with the ultrasonic detection device and the DOT detection device is used for imaging the breast by simultaneously generating functional images and structural information images of the breast based on the imaging.

3 Claims, 7 Drawing Sheets

Working flow chart of the DOT ultrasonic fusion system

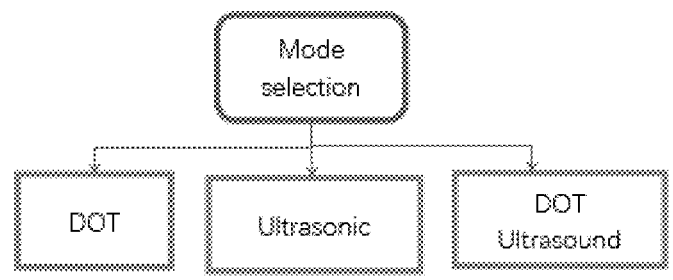
Figure 1 Mode selection schematic diagram
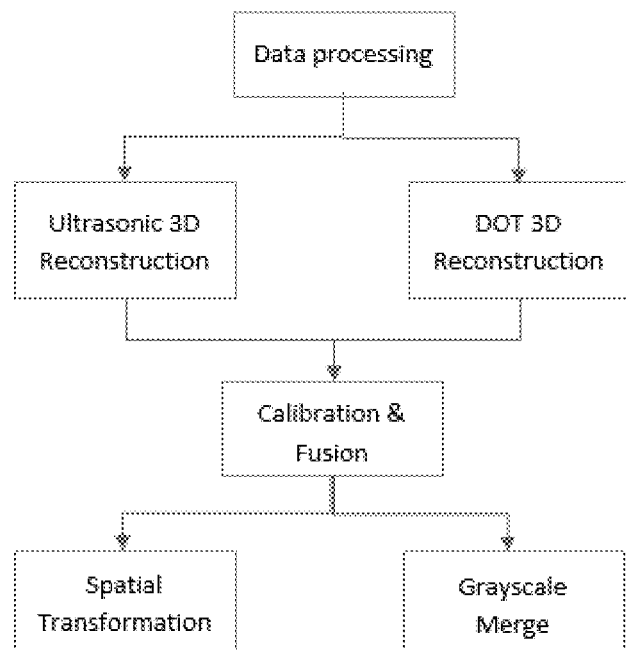
Figure 2 Functional schematic diagram of the DOT ultrasonic fusion imaging system

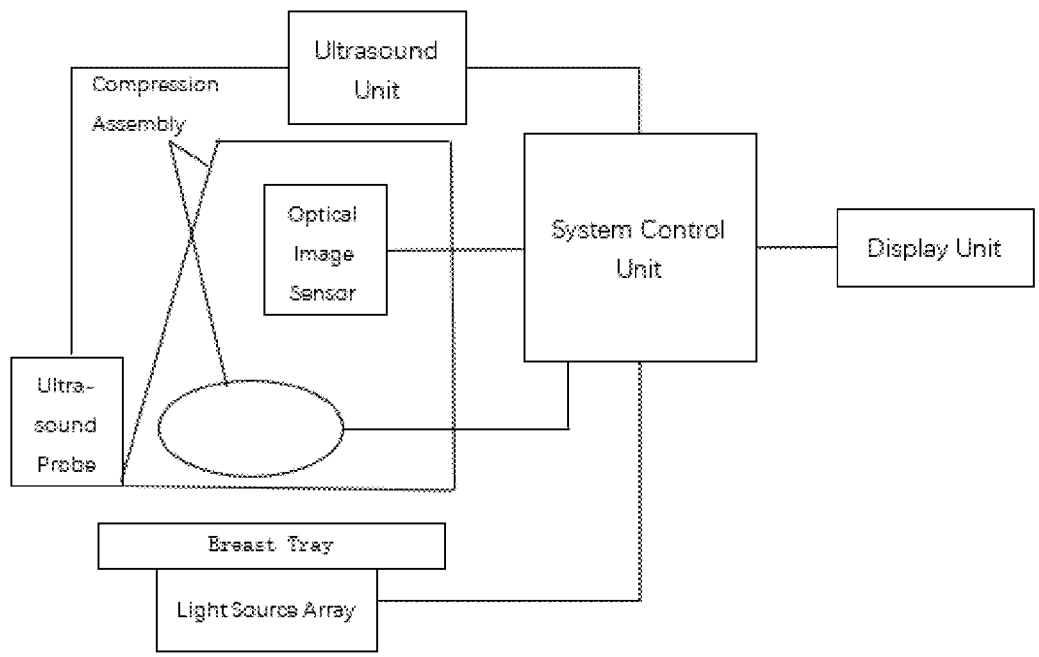
Figure 3 Block diagram of the DOT ultrasound fusion imaging system
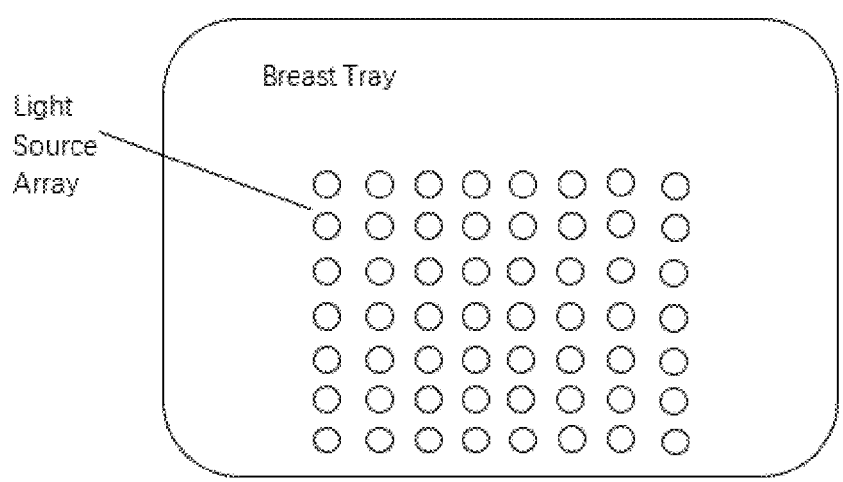
Figure 4 Schematic diagram of the breast tray and the light source array

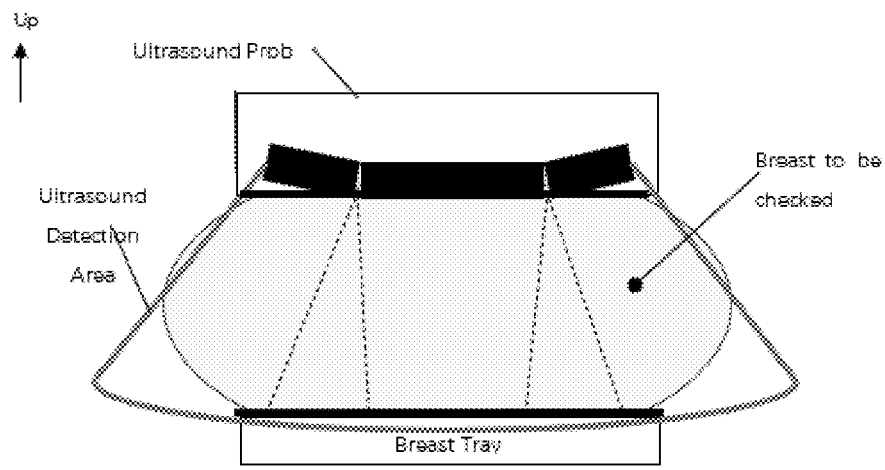
Figure 5 Face-up view of the ultrasonic detection area
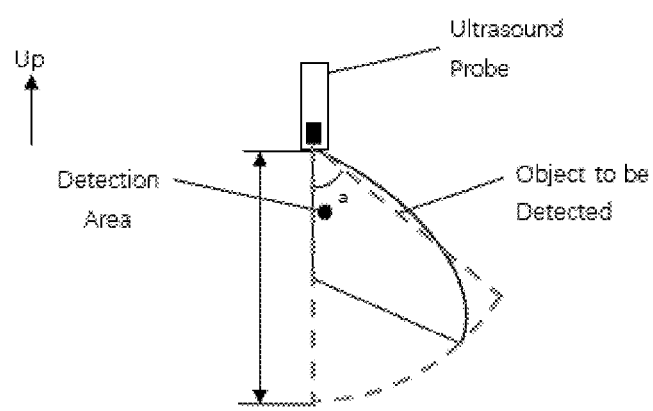
Figure 6A Side view of the ultrasonic detection area

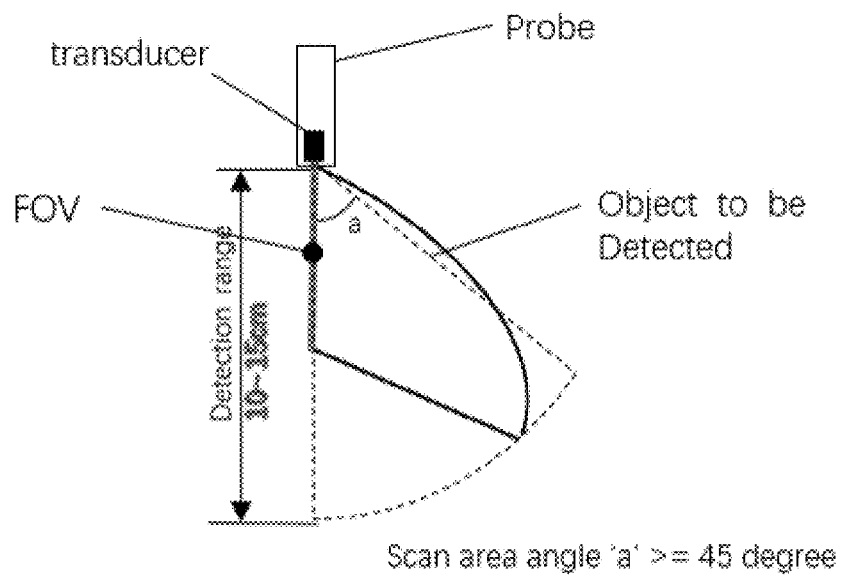
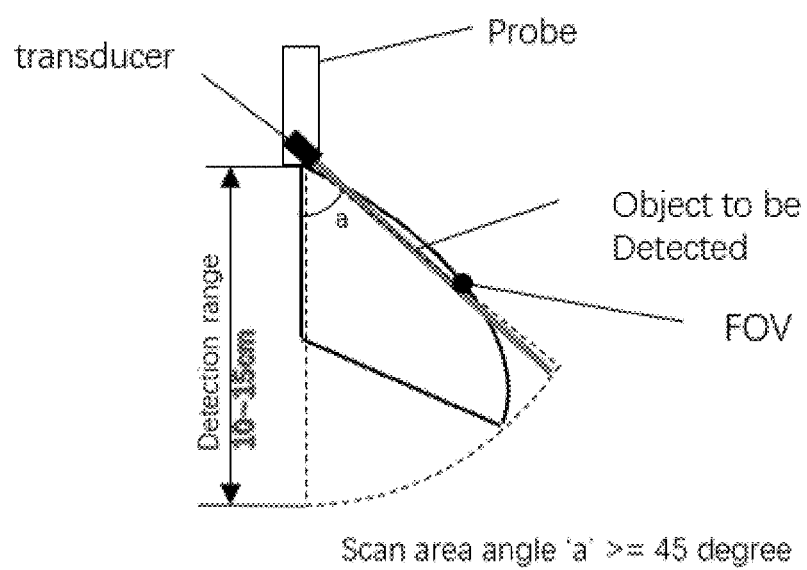
Figure 6B FOV side view - Scan angle range

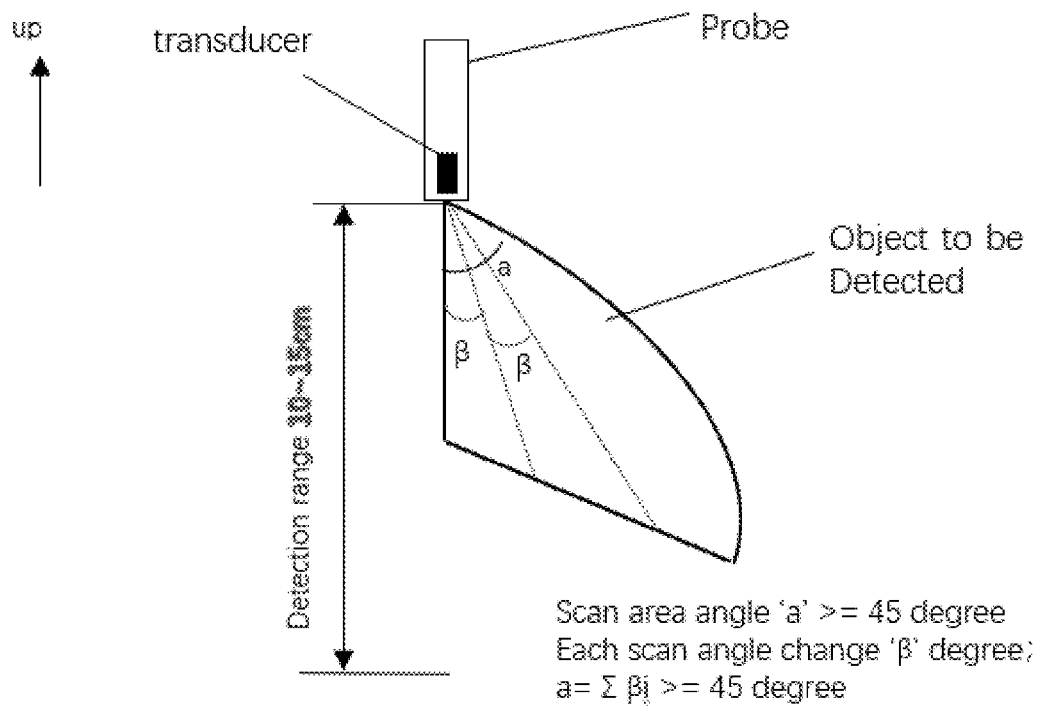
Figure 6C FOV side view - Scan angle changes step by step
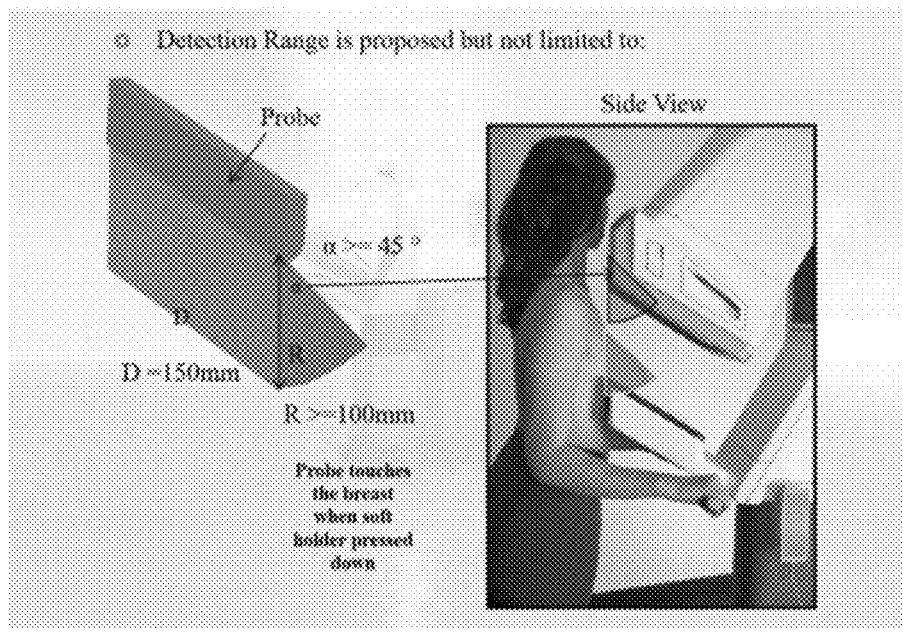
Figure 7 Schematic diagram of human breast placement

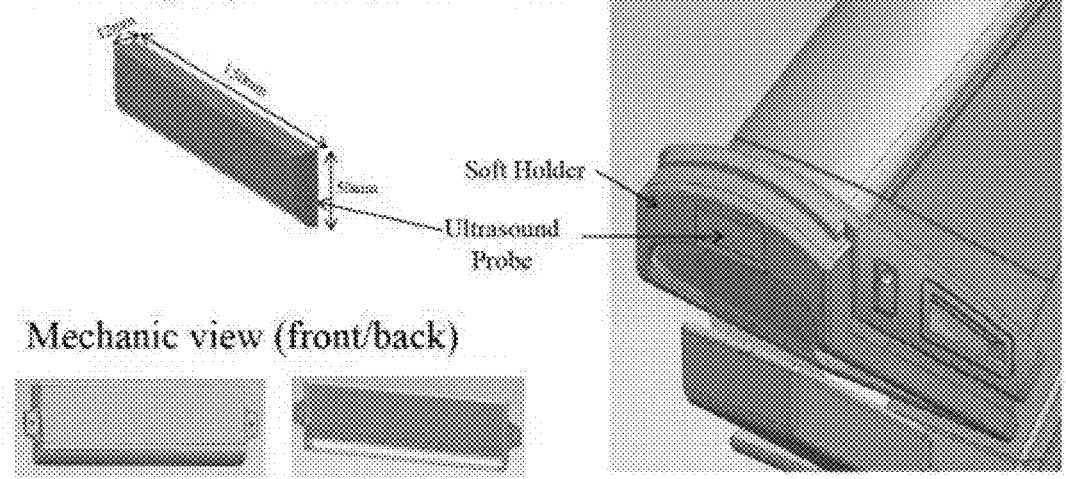
Figure 8 Hardware schematic diagram of the dynamic DOT imaging module combined with the ultrasonic imaging module
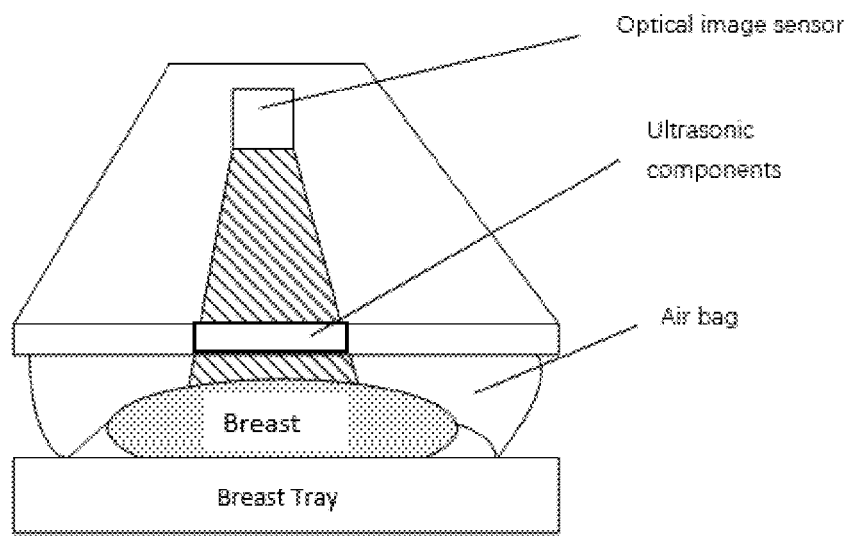
Figure 9 Schematic diagram of the breast compression assembly

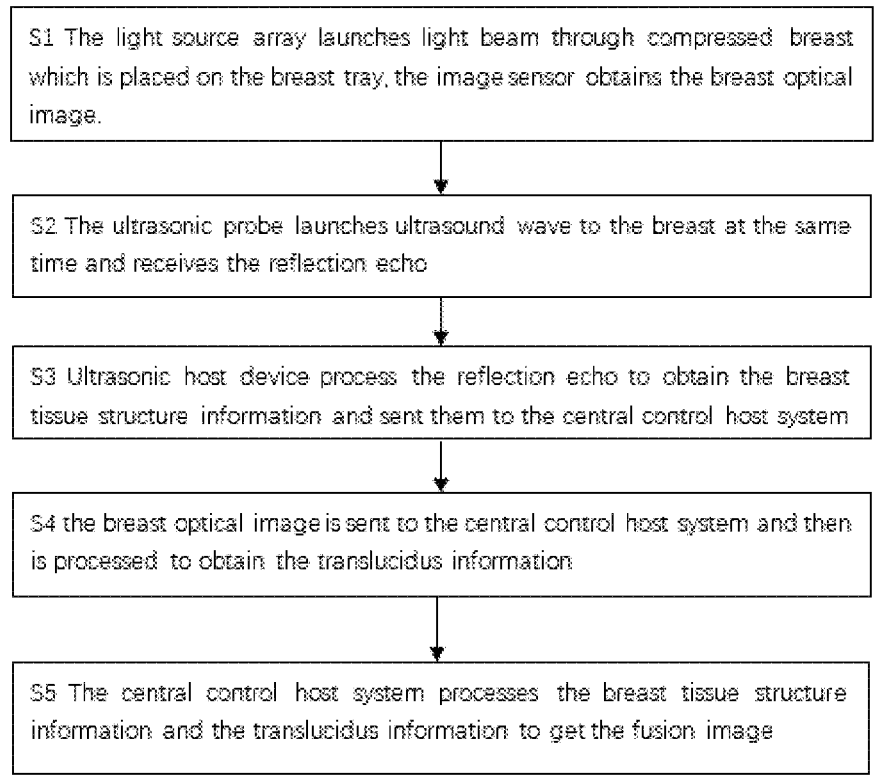
Figure 10 Working flow chart of the DOT ultrasonic fusion system

DUAL MODE THREE-DIMENSIONAL BREAST IMAGING DEVICE AND METHOD

CROSS REFERENCE TO RELATED APPLICATIONS

This application claims priority to and the benefit of U.S. Provisional Patent Application No. 63/276,345, filed on Nov. 5, 2021, and titled, "DUAL MODE THREE-DIMENSIONAL BREAST IMAGING DEVICE AND METHOD", the contents of which are incorporated herein by reference in its entirety.

BACKGROUND

Breast cancer has now become the first morbidity and fifth mortality rate among women. According to clinical statistics, early breast tumors can reach more than 90% cure rate through surgery, while the middle and late stage is highly fatal. Therefore, to be able to detect early breast tumors through screening is of great significance for women's health. Existing breast tumor examination methods include mammography MRI (magnetic resonance imaging), PET (positron emission tomography), ultrasound, DOT (diffuse optical tomography) and many other technologies. Among them, MRI and PET inspection is expensive, mammography inspection has radiation and low specificity, making it difficult to carry out large-scale screening application. Ultrasound is a structural imaging technology, which can well describe the structure of the focal point, but it cannot detect small calcification points, and it is difficult to tell the difference between benign and malignant tumor. DOT is a new generation of non-invasive functional image tumor detection technology. It has gradually emerged in recent years due to its advantages of high sensitivity and high specificity.

The present invention, ultrasound and dynamic DOT fusion imaging system, combines the DOT breast functional imaging technology with the structural imaging advantages of ultrasound to create a new generation of multimodal breast screening and diagnostic systems.

According to theory of tumor angiogenesis, mass capillaries grow when tumors develop to 2 mm, dynamic DOT breast tumor detection techniques are targeting the tumor angiogenesis, by applying specific pressure to the breast tissue and scanning the breast using near-infrared light, obtaining the spatial information of the breast through image reconstruction technology, to detect the dynamic changes of the spatial distribution and absorption of deoxyhemoglobin in specific spectra. Meanwhile, the invention using B-type ultrasound imaging technology, obtaining the structural images of the breast tissue. Combining the functional information of DOT images and structural information of ultrasound images, using intelligent diagnostic technology, early breast tumors (2 mm) and their benign and malignant attributes can be effectively identified. The system is easily to be operated; the scan time is short. It combines ultrasonic scan imaging and dynamic DOT scanning imaging, which can greatly improve the efficiency of breast cancer screening.

SUMMARY

An object of the present disclosure is to provide a dual-mode 3D breast imaging device and a fusion method. In an illustrative embodiment, the disclosed device uses ultrasonic wave, visible red light or near-infrared light synchronous scanning. It can display the 3-dimensional structural ultrasonic image and diffusion optical image of the breast.

An ultrasonic detection device and a DOT detection device which can detect the changes of breast blood oxygen detection device of the system are connected to a host machine.

In an illustrative embodiment, a breast examination device includes a breast tray assembly, and LED light array board. It has an ultrasonic examination module capable of phased array scanning. According to an aspect of the present disclosure, a breast to be checked is put on the tray and is slightly compressed by an airbag. By combining the disclosed dynamic DOT module and ultrasound module, functional imaging and structural information images of the breast can be obtained at the same time. The DOT functional imaging data and ultrasonic image data are matched and integrated to form a new breast image. The new breast image has the features of DOT functional image and breast ultrasound image for the diagnosis and accurate diagnosis result. The combined image may include the tumor shape, location, size. A DOT examination module or ultrasound examination module may be selected separately to obtain separate images if desired.

BRIEF DESCRIPTON OF THE DRAWINGS

The present disclosure will now be described more fully hereinafter with reference to the accompanying drawings, in which illustrative embodiments of the disclosure are shown. Other objects, features and advantages of the present disclosure will become apparent from the detailed description, which follows when considered in light of the accompanying drawings in which:

FIG. 1 is a mode selection diagram showing optional functional modes of the disclosed imaging system;

FIG. 2 is functional schematic diagram of the DOT ultrasonic fusion imaging system according to an aspect of the present disclosure;

FIG. 3 is a block diagram of a DOT ultrasound fusion imaging system according to an aspect of the present disclosure;

FIG. 4 is a structural schematic diagram of a light source array on a breast tray provided according to an aspect of the present disclosure;

FIG. 5 is face-up view of an ultrasonic detection area according to an aspect of the present disclosure;

FIGS. 6A-6C are side views of an ultrasonic detection area according to an aspect of the present disclosure;

FIG. 7 is a diagram of depicting human breast placement in an imaging system according to an aspect of the present disclosure;

FIG. 8 is a hardware diagram of the dynamic DOT imaging module combined with the ultrasonic imaging module according to an aspect of the present disclosure;

FIG. 9 is a diagram of a breast compression assembly of an imaging system according to an aspect of the present disclosure;

FIG. 10 is a process flow diagram of a DOT ultrasonic fusion system according to an aspect of the present disclosure.

DETAILED DESCRIPTION

Referring to FIG. 1, according to an aspect of the present disclosure, the following operating modes of the system are optional:
1. DOT
2. Ultrasonic
3. DOT and ultrasonic fusion.

The disclosed mode selection scheme is as shown in FIG. 1.

A specific scheme according to an illustrative embodiment of the present disclosure is described below.

A functional schematic diagram of the disclosed DOT ultrasound fusion imaging system is shown in FIG. 2. The ultrasound module of the breast imaging system obtains the breast tissue morphological information, including the size and structure information; while the dynamic DOT module of the breast imaging system obtains the functional information of the breast. Based on the breast tissue structure information and the breast functional information, through fusion images, both sound mode and optical mode imaging are achieved. The fusion image determines tissue lesion information and the location and size of the lesion information, improves image reliability, and enhances the diagnostic accuracy.

The following clarify the purpose, technical solutions and advantages of the present application with the drawings of the present application. Persons having ordinary skill in the art should appreciate that other embodiments may be based on the present disclosure within the scope of the present application.

In related techniques, the dynamic diffuse optical tomography (DOT) system is an inexpensive and safe, accurate, and radiation-free method to detect breast cancer at early stage. Existing DOT systems can provide optical scattering information on whether there is any tumor in the breast, but it has been difficult to determine the location and size information of the tumor causing low reliability and low accuracy of the diagnosis. The present disclosure solves the problem by providing both morphological and functional information. FIG. 3 shows the Block diagram of the DOT ultrasound fusion imaging system according to an aspect of the present disclosure.

Module Description
1. Breast Tray—is used to hold the human breast. The light source beam can enter the human breast through the breast tray;
2. Light Source Array—set under the breast tray to transmit a beam against the breast in a preset mode;

The near-infrared light in the present embodiment is emitted by the light source array, and the near-infrared light array could be a LED array or a laser array, and the system will select a preset number of lights according to the size and position of the breast to be checked. For further elaboration of the light source array, refer to FIG. 4, a structural schematic diagram of a light source array on a breast tray provided in the embodiment of the present application. The arrangement and quantity of light sources in the light source array can be customized. The light source array can be a laser array or a LED array, where the LED array can emit red or near-infrared or infrared light. The near-infrared light in the present embodiment is emitted by a LED light array, and the system will select a preset number of LED lights according to the size and position of the breast.

3. Breast compression component—is used to apply a preset pressure on the breast;
4. The ultrasonic probe assembly—placed at the outer edge of the breast compression assembly. It is to transmit the ultrasound, and receive the echo ultrasound which contains information of the breast tissue structure;

For further elaboration of the ultrasonic assembly, the present embodiment does not define the ultrasonic assembly. The ultrasonic probe could be an ultrasonic probe set, and there is no limited for the number and location of the ultrasonic probes in the ultrasonic probe group. The ultrasonic probe of the present invention detects the breast by the system through the sequence transmission and receiving ultrasound to obtain the tissue structure information of the breast. As shown in FIGS. 5 and 6A-C, the piezo resistor unit inside the ultrasonic probe can transmit ultrasonic wave in different directions and shapes, and then receives the reflected ultrasonic information, breast tissue structure information, specifically, determine the acoustic resistance and depth of different tissues according to the ultrasonic back and forth time to obtain breast tissue structure information.

5. Image Sensor—is used to collect the breast imaging when the light source array emits a preset beam through the breast which is being compressed by the breast compression assembly;

Further elaborated for the image sensor, when a preset beam (near infrared or laser) beam illuminates the breast, the malignant tumor vessels have different optical absorption characteristics from the normal tissue and the CCD camera with the image sensor records such information. However, the location and size information of the tumor is not determined by this method alone. The ultrasound components are providing auxiliary information to determine the location and size information. The near-infrared light in the present embodiment is emitted from the near-infrared light array, and the system will select a number of LED lights according to the size and position of the breast. In this embodiment, the emission sequence of the LED array is set by the system program to illuminate the breast, while the breast is being compressed by the breast compression assembly. The CCD camera collects the breast image with optical absorption characteristics information and then through reconstruct algorithm to form an 3D functional image.

6. The ultrasonic host—connected to the ultrasonic probe assembly which control the ultrasonic component to send specific ultrasonic signals, and to receive the echo signals, to convert it into an ultrasonic image containing information of the breast tissue structure;
7. The system control unit—connected to the image sensor which control the image sensor for image acquisition, receive the breast transmission information optical image generated by the image sensor, receive the ultrasonic image generated by the ultrasonic host, and combine the ultrasonic image with the optical image to obtain the fusion image. The present embodiment does not describe the image generation methods and the image fusion methods, please refer to the relevant techniques.

Further, the system control unit is also used for receiving the breast detection command, based on the command, set the light intensity and control the light source array to turn on and off; correspondingly, the light source array transmit the preset light beam according to the command.

Further, the system control unit is also used to process the lesion area in the fusion image and add the color to the fusion image. Correspondingly, the breast imaging system also includes a display device for displaying color fusion images.

In this embodiment, the lesion area color processing, highlight the lesion features, so that the user can view the image intuitively. The present embodiment does not define the color processing, it only highlights lesion area. Further, the color fusion image is displayed on the display device. when the mouse moves to the area of the lesion in the fusion image, the relevant parameters, including but not limited to the maximum length, area, of the image will be displayed.

Embodiments of the present disclosure may also include one or more of the following options:

8. The light source array can be a LED light array or a laser array.
9. The image sensor can be a CCD camera or a CMOS camera.
10. The ultrasonic assembly is an ultrasound probe set.
11. The ultrasonic assembly can be rotated at an angle to form a scanning sector.
12. The ultrasonic components can send ultrasonic signals and receive them at certain angles.
13. The system control unit can extract the features from the ultrasonic image, and extract the features from the light image, matching the first feature with the second feature, and performing image processing so that the fusion image is obtained.
14. The system control unit can process the lesion features in the fusion image to obtain the color fusion image.
15. The display device can display the fusion image in color.

Human breast placement involving DOT and ultrasound fusion imaging system is shown in FIG. 7.

The hardware schematic diagram of the DOT ultrasonic fusion imaging system is as shown in FIG. 8.

Further, in an illustrative embodiment, the breast imaging system also includes: an air bag configured for compressing the breast. Referring to FIG. 9, a schematic diagram of breast placement provided for this embodiment of the present application, wherein during image acquisition, the breast is placed on the breast tray, the air bag is used to compress the breast, and the image sensor collects the breast image when the light source array emits a preset beam through the breast. The present embodiment does not define the material of the breast compression assembly, as long as the purpose of the present embodiment can be achieved.

According to Another Aspect of the Present Disclosure, Present Application Provides a Breast Imaging Method.

The breast imaging system provided in this embodiment obtains breast tissue structure information from the ultrasound module, which obtains the morphological information about the breast, including the size and structure information. It also collects the functional information through the image sensor. The ultrasonic and optical images generated according to the breast tissue structure information and the breast light transmission information are integrated, to form the fusion images. Breast images with both morphological and functional information were obtained. According to an aspect of the present disclosure, such fusion images can be used to determine tissue lesion information and also the location and size of the lesion, with improved image reliability, and enhance the diagnostic accuracy.

A workflow flow chart illustrating this aspect of the disclosure is shown in FIG. 10. When the light source array under the breast tray emits a preset beam, the image sensor collects information about diffuse light through the breast tissue. The ultrasonic assembly emits the ultrasonic signal at the same time. The ultrasonic assembly receives a reflection echo containing the breast tissue structure information. The ultrasonic unit receives the reflection echos from the ultrasonic assembly, convert them into images, then sends them to the system control unit. The system control unit receives the light image from the image sensor, and the ultrasonic image from the ultrasonic unit, then perform image registration and fusion to obtain the fusion image.

Based on the above technologies, the breast imaging method provided in this embodiment obtains breast tissue structure information from the ultrasound component. The obtained morphological information about the breast includes the size and structure information. The optical image sensor collects the breast light transmission information which include the functional information of the breast tissue structure.

Further, according to an aspect of the present disclosure, the system control unit may be used to process the lesion features in the fusion image and obtain color fusion images. In an illustrative embodiment, the disclosed breast imaging system also includes a display device for displaying the color fusion images.

In this embodiment, the lesion features go through a color processing process that highlights lesion features and thereby facilitate the user to intuitively obtain useful information from the images. The present embodiment does not require a particular method of color processing, as long as the lesion features can be highlighted and the color fusion image cam be displayed on the display device. In an illustrative embodiment, when a user moves the mouse or other pointing device to an area of the lesion feature in the color fusion image, the relevant parameters can be displayed.

The embodiments in this case are described in a progressive manner. Persons skilled in the art should appreciate that the exemplary units and algorithm steps described herein can be realized by a various combinations of electronic hardware, computer software or both. In order to clearly explain the interchangeability of the hardware and software, the composition and steps of the respective examples have been generally described in the above description. Whether these functions are performed in hardware or software manner depends on the specific application and design constraints of the technical scheme. Different methods may be used to implement the described functions for each particular application, but such an implementation should not be considered beyond the scope of the present application.

A breast imaging system and a breast imaging method provided in the present application are described herein. The described principles and embodiment of the application are provided to help the reader understand the method and implementation of the application and its core ideas. It should be appreciated by ordinary technicians in the technical art of the present disclosure, several improvements and modifications of the embodiments described herein may rely on principles of the present disclosure and may fall within the scope of protection of the claims of the present application.

What is claimed is:

1. A dual mode imaging apparatus for 3D breast tissue imaging measurements of functional and structural breast conditions, comprising:
   (a) a diffuse optical tomography (DOT) detection device with a supporting transparent plate adjacent an edge of the breast to be imaged, means for compressing the portion at that edge of the breast, the DOT comprising an array of LEDs on a distal side of the sheet from the compressed edge portion, with the LEDs of the array selectively or collectively emitting red or near infrared lights from LEDs of the array through the plate to and through the plate and breast tissue adjacent the edge portion and a probe for receiving diffusively attenuated and refracted emissions signals to a camera sensor to image breast absorption characteristics;

(b) an ultrasonic detection device separate from the DOT device comprising means to create and transmit ultrasonic waves from one or more edge portions of the breast other than the edge occupied by the transparent support plate serving as passage for the LED light and a probe means to capture ultrasonic waves as modified in transiting the breast tissue in wave paths to capture with the DOT detected structural and functional characteristics of masses to be examined and constructed for capturing different angled areas of fields of view in the breast;

(c) a host system control unit in communication with each of the ultrasonic detection device and the DOT detection device, to fuse and create a display of overlaid captured waves of the emissions DOT and ultrasonic unit combining the echoed ultrasonic image with the DOT optical image wherein the DOT detection device and ultrasonic detection device externally generate respective simultaneous functional and structural measurements combined for creating as a combined dual mode three dimensional breast image to detect changes of tissue blood oxygen, and other functional and structural aspects of the breast;

(d) wherein neither of the DOT and ultrasonic devices activates the other when their respective waves transit the breast.

2. A breast imaging method comprising the steps of:
imaging a breast using diffuse optical tomography (DOT) detection and ultrasound detection each emitting and detecting light and sound reflections separately,
combining them to generate fused functional images and structural location/morphology images of the breast based on the respective DOT and ultrasonic captures,
wherein the DOT detection illuminates the breast and captures structural optical absorption characteristics of masses within the beast and the ultrasound detection shows location, morphology and size information.

3. The method of claim 2 wherein the DOT detection is implemented by a red or near infrared planar array of LEDs and the ultrasound detection by a probe set that constructed and arranged to pass though the breast in different directions of fields of use emitting separate waves from different breast edge portions and rotating to capture in view.

* * * * *